(12) United States Patent
Firsov (10) Patent No.: US 7,654,973 B2
(45) Date of Patent: Feb. 2, 2010

(54) ORTHOTIC BRACING DEVICE

(76) Inventor: Igal Firsov, Tnuat Hamery 4, Kiryat Ono 55286 (IL)

( * ) Notice: Subject to any disclaimer, the term of this patent is extended or adjusted under 35 U.S.C. 154(b) by 328 days.

(21) Appl. No.: 11/579,013

(22) PCT Filed: Apr. 21, 2005

(86) PCT No.: PCT/IL2005/000421

§ 371 (c)(1),
(2), (4) Date: Oct. 30, 2006

(87) PCT Pub. No.: WO2005/105004

PCT Pub. Date: Nov. 10, 2005

(65) Prior Publication Data

US 2008/0021357 A1  Jan. 24, 2008

(30) Foreign Application Priority Data

Apr. 29, 2004  (IL) .................................... 161687

(51) Int. Cl.
*A61F 5/00* (2006.01)
(52) U.S. Cl. .......................... 602/19; 128/869; 128/876
(58) Field of Classification Search .................. 602/19; 128/869–870, 873–876; 5/624, 625, 627
See application file for complete search history.

(56) References Cited

U.S. PATENT DOCUMENTS

| 4,112,935 | A | * | 9/1978 | Latypov et al. ............... 606/54 |
| 5,031,639 | A | * | 7/1991 | Wolfer ........................ 128/874 |
| 5,048,134 | A | * | 9/1991 | Dennill et al. ................. 5/625 |
| 5,337,758 | A | * | 8/1994 | Moore et al. ................ 600/594 |
| 6,363,936 | B1 | * | 4/2002 | McCormick et al. ........ 128/870 |

FOREIGN PATENT DOCUMENTS

| DE | 94 02 629 U1 | 7/1994 |
| EP | 0 770 372 A | 5/1997 |
| FR | 2 825 265 A | 12/2002 |
| WO | WO 03/037238 A2 | 5/2003 |

* cited by examiner

Primary Examiner—Michael A. Brown
(74) Attorney, Agent, or Firm—Scully, Scott, Murphy & Presser, P.C.

(57) ABSTRACT

There is provided a customizable orthotic bracing device, including an exoskeletal quasi-spinal column (12) extendable along the back of a patient and attachable to a body portion of the patient by means of a plurality of belt means (14, 14') substantially surrounding the body portion at different points thereof, with the quasi-spinal column being comprised of a plurality of stackable and interlinkable segmental units (20), each unit consisting of a number of interlinkable sub-units (22, 24, 26, 28), characterized in that the position of the sub-units relative to one another can be adjusted in at least three degrees of freedom.

16 Claims, 12 Drawing Sheets

ORTHOTIC BRACING DEVICE

FIELD OF THE INVENTION

The present invention relates to an orthotic device and, more particularly, to a customizable orthotic bracing device providing adjustable support and variable forces for treatment and rehabilitation of various disorders of the musculoskeletal and nervous system associated with abnormalities of posture, muscle tone and motor function.

BACKGROUND OF THE INVENTION

The list of disorders associated with abnormalities in muscle tone, posture, and motor function is long and includes, amongst others, such problems as cerebral palsy, scoliosis, motor pareses and paralyses (of various causes), dystonia, and injuries of the spine and joints. Such problems, even when the immediate site of pathology is localized, have far-flung consequences for the entire musculoskeletal and locomotor systems. Effective treatment and rehabilitation of such problems require complex, global therapies that take into account and have an effect on the entire musculoskeletal and locomotor systems.

Cerebral palsy is a chronic and persistent disorder of movement and posture caused by non-progressive pathological processes of the immature central nervous system. Injury to the brain may occur before, during or shortly after birth. The overall incidence in Western countries of cerebral palsy is between 1.5 and 2.5 per 1000 live births. An estimated 500,000 to 700,000 children and adults in the United States manifest symptoms of cerebral palsy and about 9,000 new infants develop the disorder annually. Management of the child with cerebral palsy is a complex challenge.

Physiotherapy is the principal non-surgical form of treatment. Its aims are to prevent contractures and deformities and to promote functionally useful posture and movements. Cerebral palsy is typically associated with spasticity of muscle that results in the limb being held in abnormal postures. Because muscle growth depends to a certain extent on muscle stretch, if abnormal postures are maintained for extended periods, muscle growth will be impaired. Eventually, the muscle will become short and contractures will develop. Further, abnormal muscle movements tend to interfere with joint function. As a result, affected children may develop deformities, for example, of the foot or of the hip joint (which may become dysplastic or eventually completely dislocated). In general, such deformities can be minimized or prevented by splinting to maintain the joints and muscles in certain more natural positions, often designed to restrict rotational movement about a joint and providing active resistance to rotation.

Several prior-art devices attempting to deal with the above-mentioned problems are extensively discussed in PCT-document WO 03/037238 A2, which is incorporated herein by reference.

As distinguished from the above PCT document, the device according to the present invention is free of the encumberment of a wheel-mounted frame, while providing supportive elements that are adjustable with four degrees of freedom and adaptable to follow the spinal column of the individual patient.

DISCLOSURE OF THE INVENTION

It is thus one of the objects of the present invention is to overcome the drawbacks and disadvantages of the prior-art devices and to provide an orthotic device that is customizable and once fitted and adjusted is easy to wear, comfortable and yet offers ample support and pressure when and where needed.

According to the invention, this is achieved by providing a customizable orthotic bracing device, comprising an exoskeletal quasi-spinal column extendable along the back of a patient and attachable to a body portion of said patient by means of a plurality of belt means substantially surrounding said body portion at different points thereof, with said quasi-spinal column being comprised of a plurality of stackable and interlinkable segmental units, each unit consisting of a number of interlinkable sub-units, characterized in that the position of said sub-units relative to one another can be adjusted in at least three degrees of freedom.

BRIEF DESCRIPTION OF THE DRAWINGS

The invention will now be described in connection with certain preferred embodiments with reference to the following illustrative figures, so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF PREFERRED EMBODIMENTS

Figure 1:
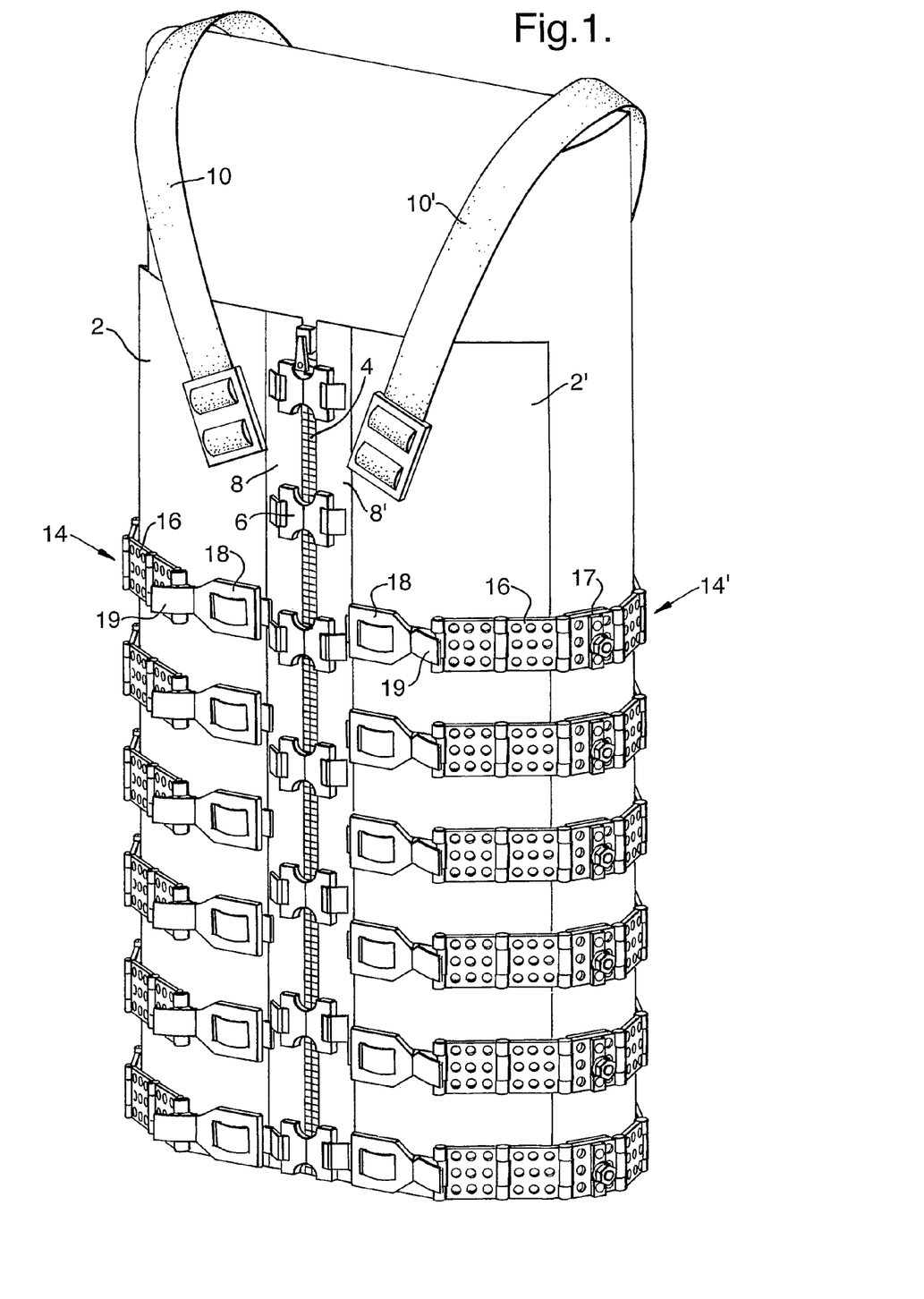
FIG. 1 is an isometric view of the device as mounted on a schematized human torso.

Referring now to the drawings, there is seen in FIG. 1 a split breast plate 2, 2', contacting the front of the patient's schematized body portion, e.g., torso T. Split plate 2, 2' is advantageously made of a canvas-type fabric and can be joined by means of a zipper 4 facilitating the donning and doffing of the entire device. To protect the closed zipper 4 against excessive lateral forces, there are provided a number of snap-in clasps 6 fixedly attached to base strips 8, 8' of zipper 4 that must be opened before zipper 4 can be unzipped.

Also seen are a pair of straps 10, 10' slung over the patient's shoulders and fixedly attached to the uppermost member of the exoskeletal quasi-spinal column 12 (FIG. 3) that is a central component of the device according to the invention and extends along the patient's back.

Further seen are a number of belt elements 16 constituting pairs of belt halves 14, 14', which between themselves, substantially surround torso T. Each belt half is comprised of a plurality of belt elements 16 hingedly articulated to one another and shown to better advantage in, and discussed in conjunction with, FIGS. 24 and 25.

The front ends of belt halves 14, 14' are articulated to buckles 18 having straps 19 by means of which belt halves 14, 14' can be tightened. Certain belt elements 17 are of a special design discussed in conjunction with FIGS. 21 to 23.

Figure 3:
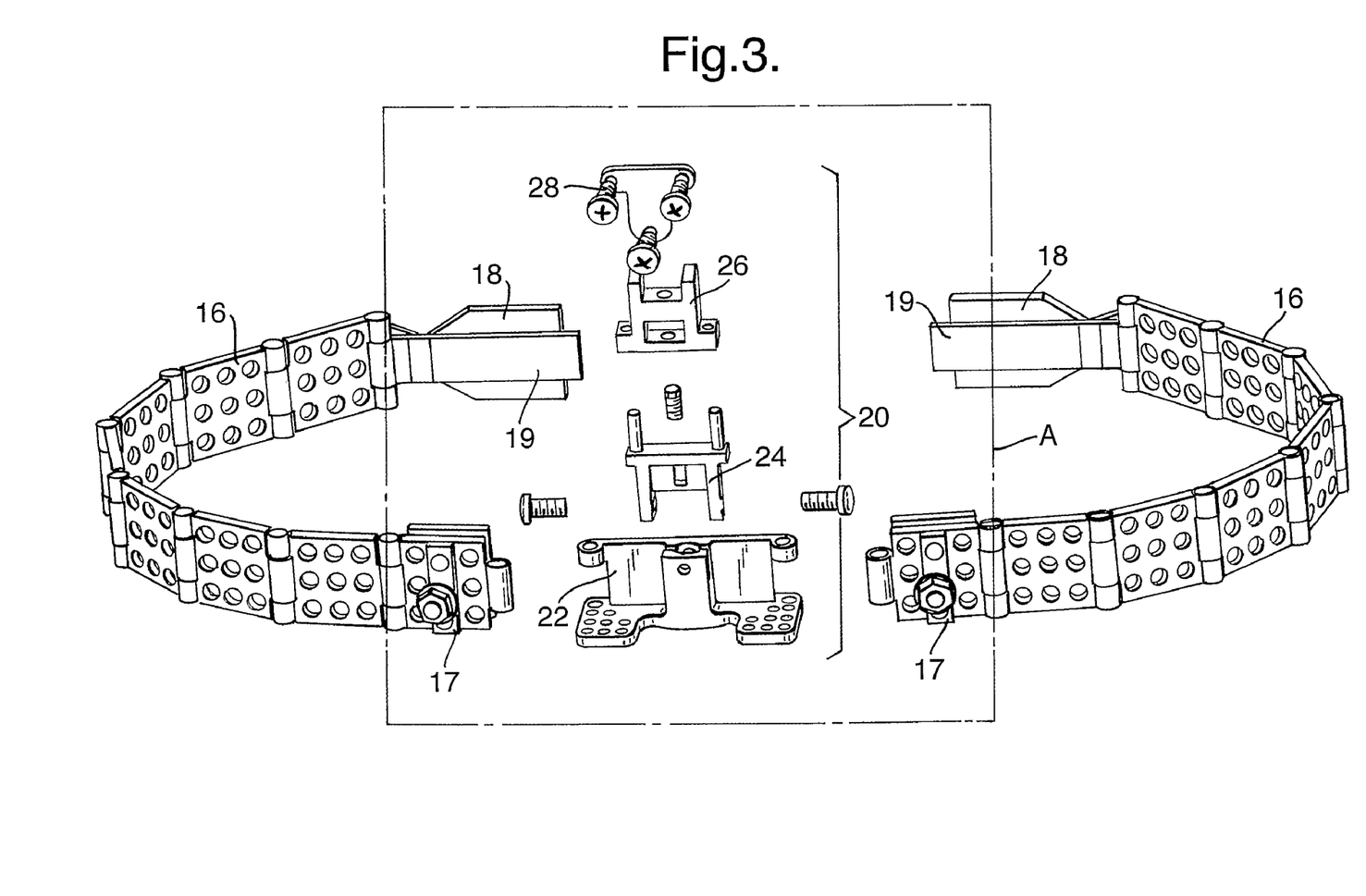
FIG. 3 shows an exploded view of one of the segments of the segmented column of the device, including one of the belts.
Figure 4:
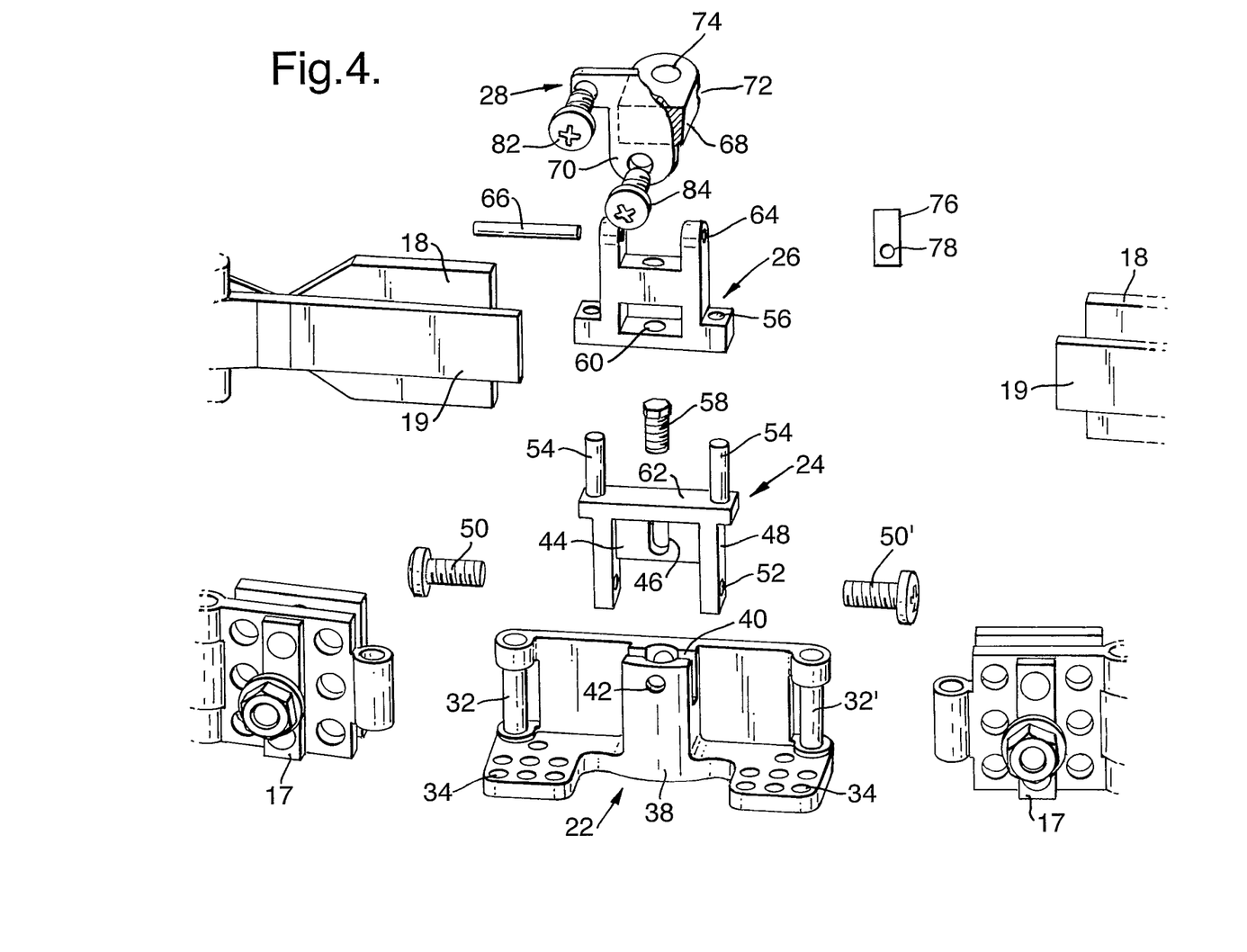
FIG. 4 is an enlarged view of the components included in square A of FIG. 3.

FIGS. 3 and 4 represent the rear view of the device. There is seen the segmented spinal column 12 which, in this embodiment, is made up of six segmental units 20 (see FIG. 3), each segmental unit consisting of four sub-units: 22, 24, 26 and 28. The uppermost sub-unit 28 carries a cross-bar 30 to which are fixedly attached the rear ends of shoulder straps 10, 10'. The rear ends of belt halves 14, 14' are articulated to sub-units 22 by means of hinge pins 32, 32' (FIG. 4).

The entire column 12 is held together by a plurality of elastically deformable biasing means 35, such as rubber cords or helical tension springs, threaded through holes 34 of sub-units 22 (FIG. 2), anchored in uppermost sub-unit 22 and, after being imparted on initial tension, being clamped fast by lockable clamps 36 located below lowermost sub-unit 22. These cords or springs oppose all flexing, tilting or twisting movements of column 12, tending to restore the original, straight state of column 12.

Figure 7:
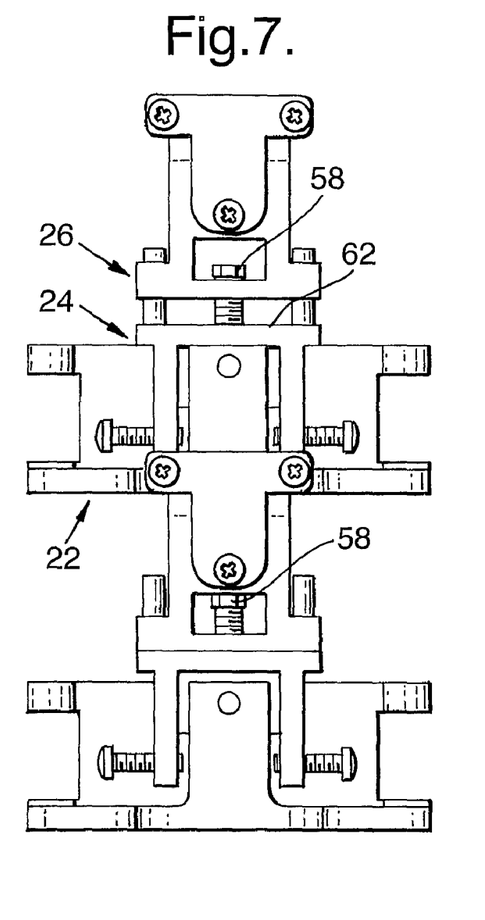
FIG. 7 is a frontal view of sub-units of segments of the segmented column, showing the possibility of translational movement between the sub-units of a segmental unit.
Figure 8:
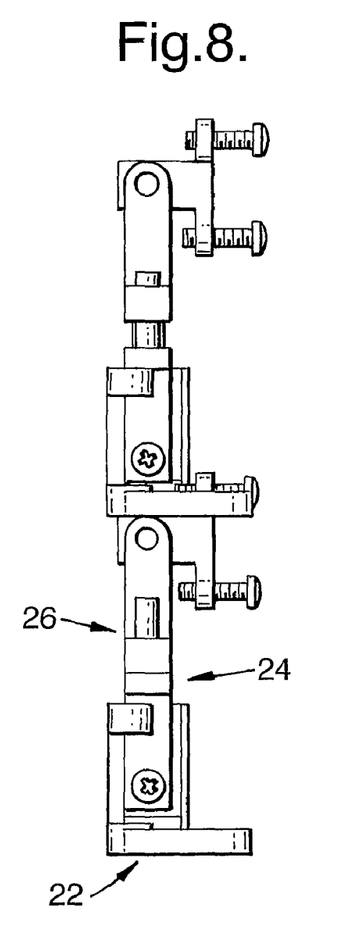
FIG. 8 is a side view of the segments of FIG. 7.
Figure 9:
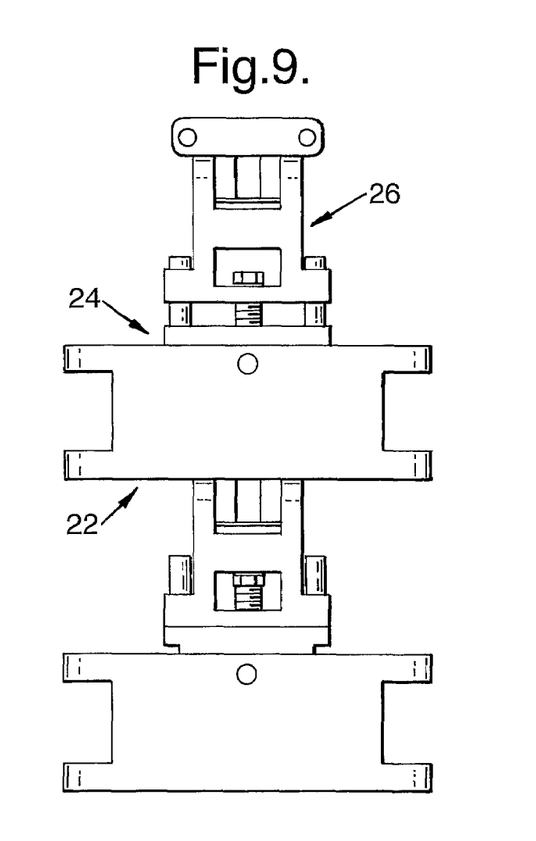
FIG. 9 depicts a rear view of FIG. 7.
Figure 10:
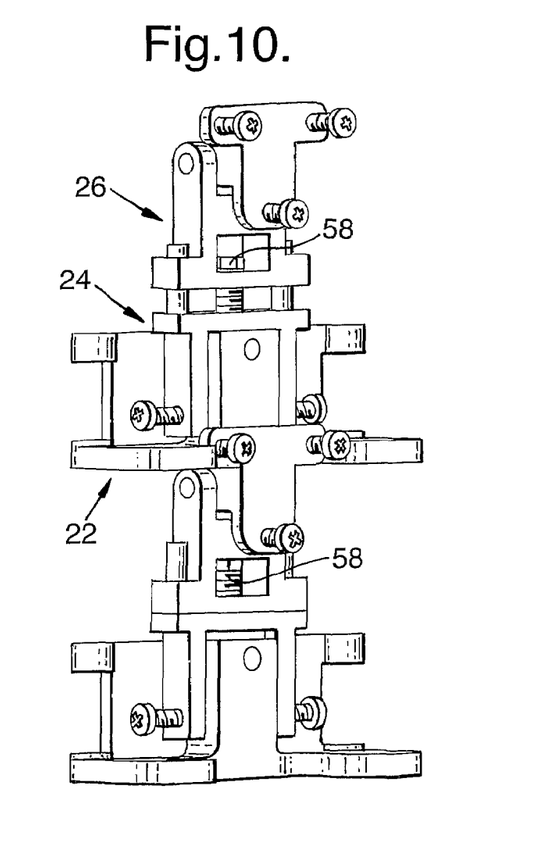
FIG. 10 is an isometric view of FIG. 7.

Also seen in FIG. 4 as part of sub-unit 22 is a central prismatic projection 38 having a slot 40 crossed by a pin 42. Into this slot slidingly fits a wall portion 44 of sub-unit 24 having an elongated hole 46 through which, in assembly, passes pin 42 of sub-unit 22. Sub-unit 24 has thus two degrees of freedom of movement with respect to sub-unit 22: due to elongated hole 46, it can move up and down, and due to the fact that the distance between its legs 48 is longer than the width of projection 38, it can tilt laterally. Lateral tilt can be effected either by a spontaneous lateral tilt of the patient's torso, or with the aid of two screws 50, 50' fitting threaded holes 52 in legs 48 (see also FIG. 11). Further seen are also two guide rods 54 slidingly fitting holes 56 in sub-unit 26. Movement of sub-unit 26 with respect to sub-unit 24 is effected by threading screw 58 into, or out of, threaded hole 60. As can be seen in FIG. 7, threading screw 58 into threaded hole 60 causes the end of screw 58 to press against surface 62 of sub-unit 24, thereby pushing sub-unit 26 upwards. When screw 58 is turned in the counter-clockwise sense, the above-mentioned elastic means (cords or springs) 35 will restore the displaced components to their initial position.

Sub-unit 26 has two upper arms having holes 64 into which fits a rod 66 by means of which sub-unit 28 is articulated to sub-unit 26, which is seen to consist of a T-shaped front part. The latter has been partially cut in FIG. 3, to show a second, advantageously integral part of sub-unit 28, a prismatic part 68 projecting from the T-shaped front part 70. Part 68 fits the U-shaped cutout in the upper portion of sub-unit 26 and has a transverse bore 72 into which fits rod 66, thereby, in assembly, articulating sub-unit 28 to sub-unit 26.

Further seen is a vertical bore 74 into which fits a post 76 having a transverse hole 78 enabling rod 66 to pass. In assembly, post 76 projects from prismatic part 68 and fits a bore 80 provided in the underside of sub-unit 22 (see FIG. 15), thereby facilitating stacking of the segmental units 20.

Also shown are two screws 82, 82' (of which only one is seen) and one screw 84. Screws 82 are instrumental in facilitating a motion of twist (see FIG. 15), while screw 84 enables tilt in the median plane (see FIGS. 5 and 6).

Figure 5:
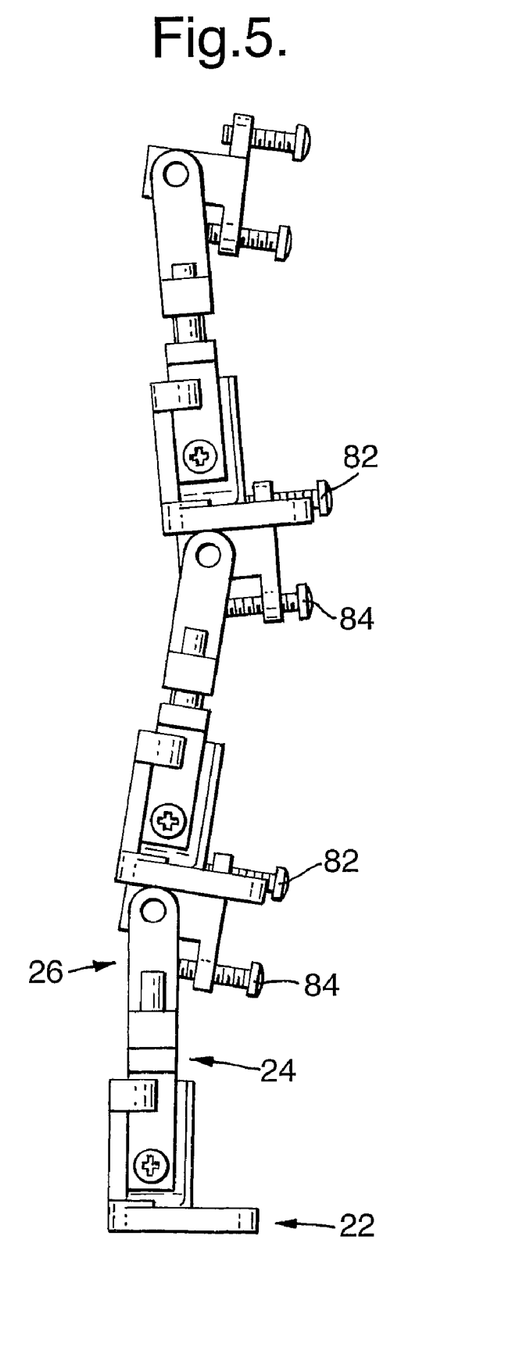
FIG. 5 illustrates a lateral view of three interlinked segments of the segmented column, showing the possibility of relative tilt of some of their components in the median plane.
Figure 6:
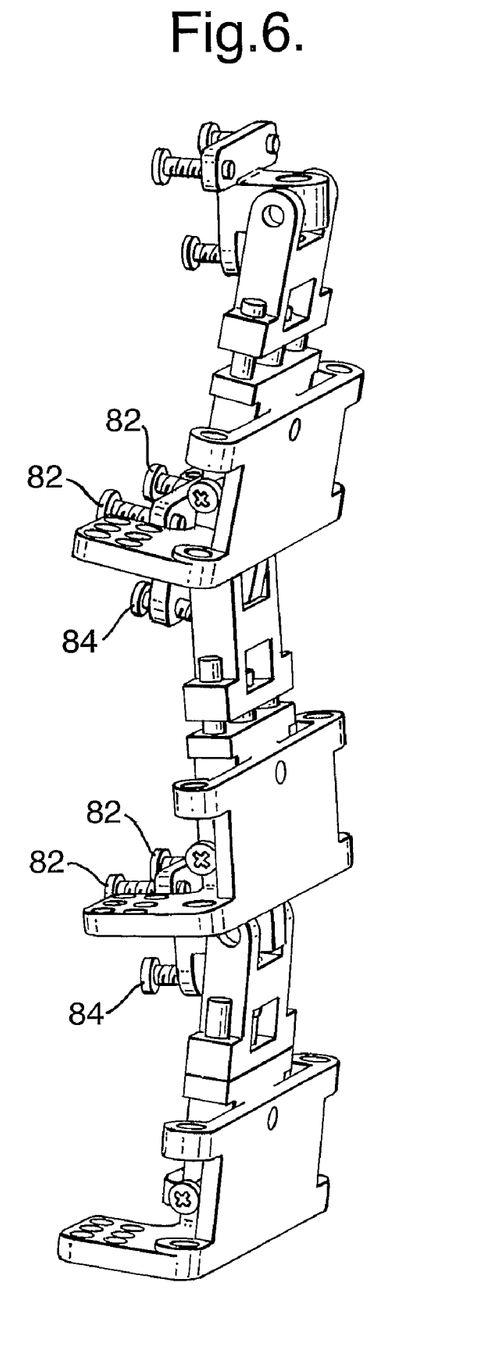
FIG. 6 is an isometric representation of the segments of FIG. 5.

FIGS. 5 and 6 illustrate the spinal column according to the invention undergoing a tilting motion in the median plane. It is seen that the segmental units undergo a tilting motion in an alternating direction when screws 84 are alternatingly withdrawn and screwed in. Clearly, such a tilting motion need not be alternating as shown, but may also be unidirectional, all according to the purpose of use or treatment.

FIGS. 7 to 10 illustrate the capability of a linear, translational movement between sub-units of segmental units. It is clearly seen that when screw 58 is tightened down, a distance is created between sub-unit 24 and sub-unit 26.

Figure 11:
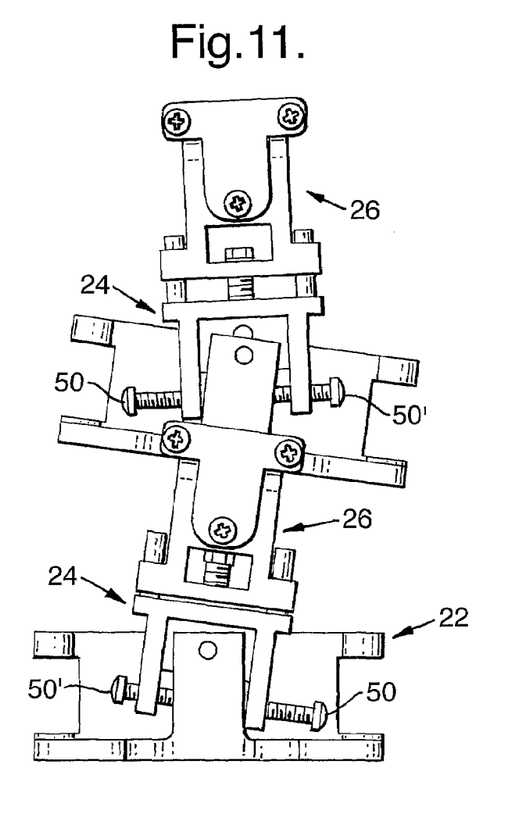
FIG. 11 is a frontal view of two interlinked segments of the segmented column, showing the capability of the column to follow the outlines of a scoliotic spine.
Figure 12:
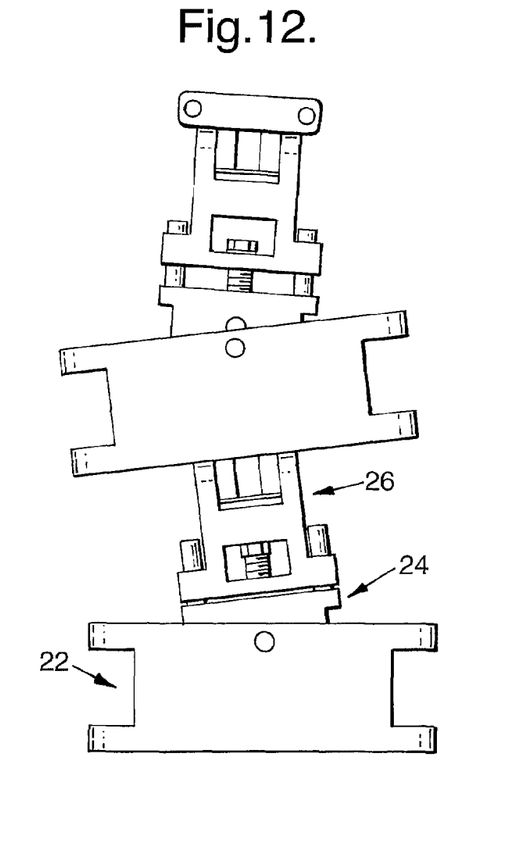
FIG. 12 is a rear view of the segments of FIG. 11.
Figure 13:
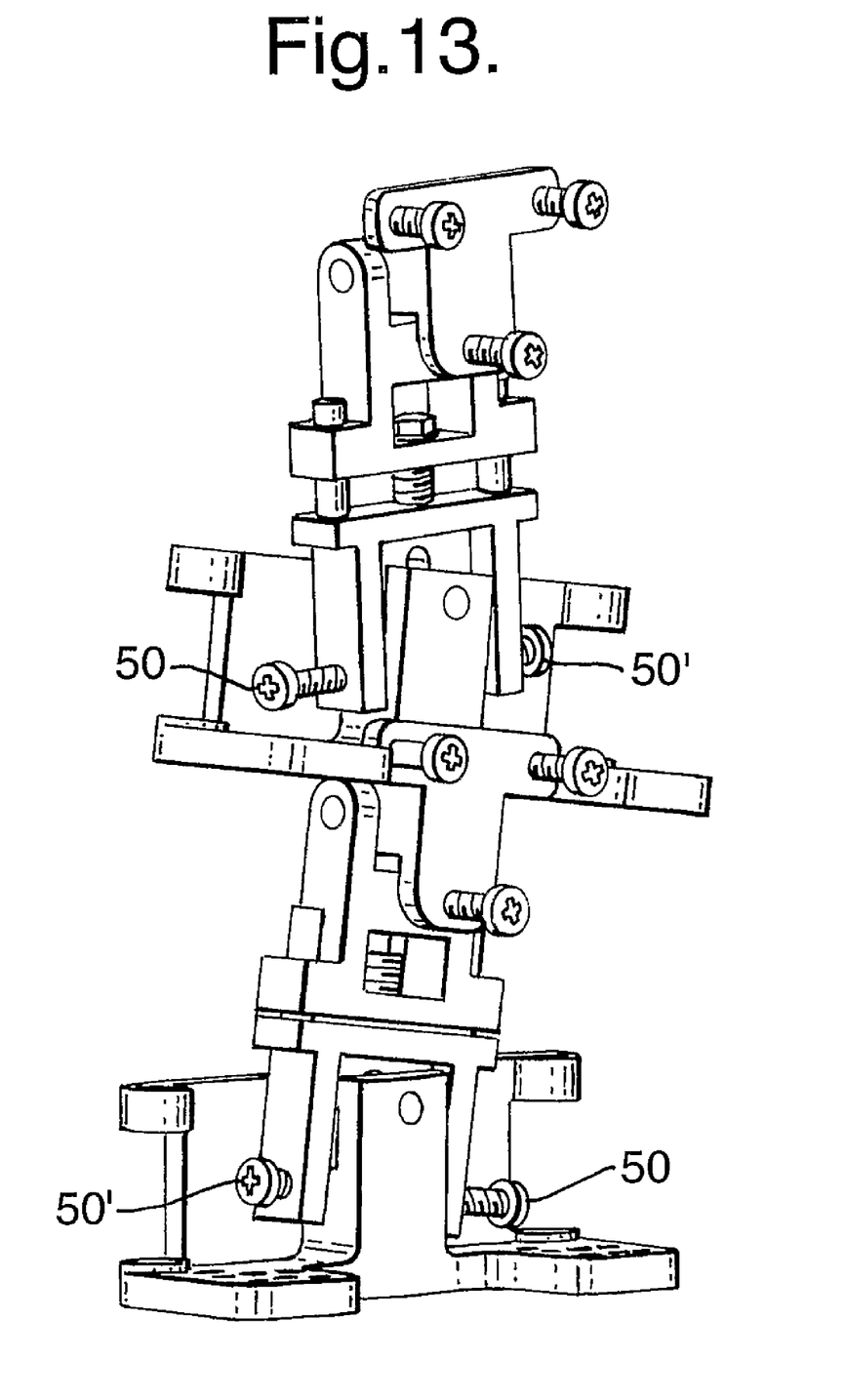
FIG. 13 is an isometric view of the segments of FIG. 11.

FIGS. 11 to 13 shown how the spinal column of the device according to the present invention can be tilted in a lateral direction, e.g., to follow the contours of a scoliotic spine. By opening lower screw 50 and closing lower screw 50' as seen in FIG. 11, lower sub-units 24 and 26 are tilted to the right, as is upper sub-unit 22, while by opening upper screw 50 and closing upper screw 50', sub-units 24 and 26 are tilted to the left.

Figure 14:
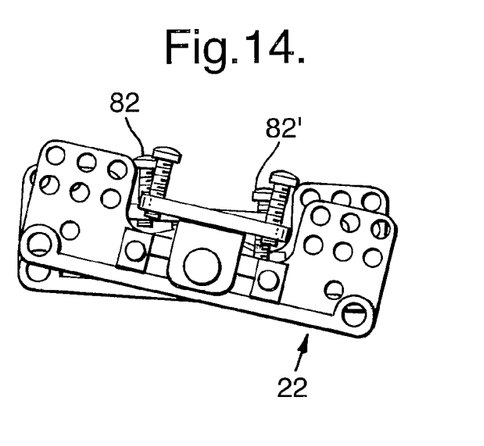
FIG. 14 is a top view illustrating the capability of the segments to perform relative twists about their longitudinal axis.
Figure 15:
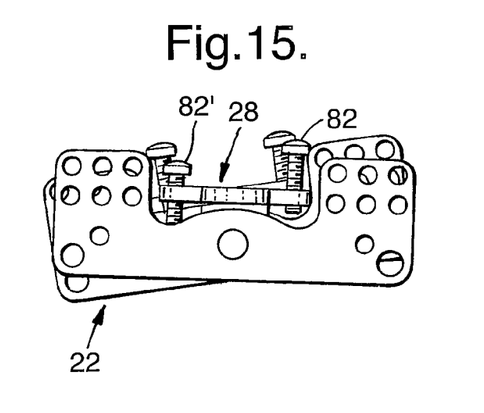
FIG. 15 is a bottom view of the segment group of FIG. 14.
Figure 16:
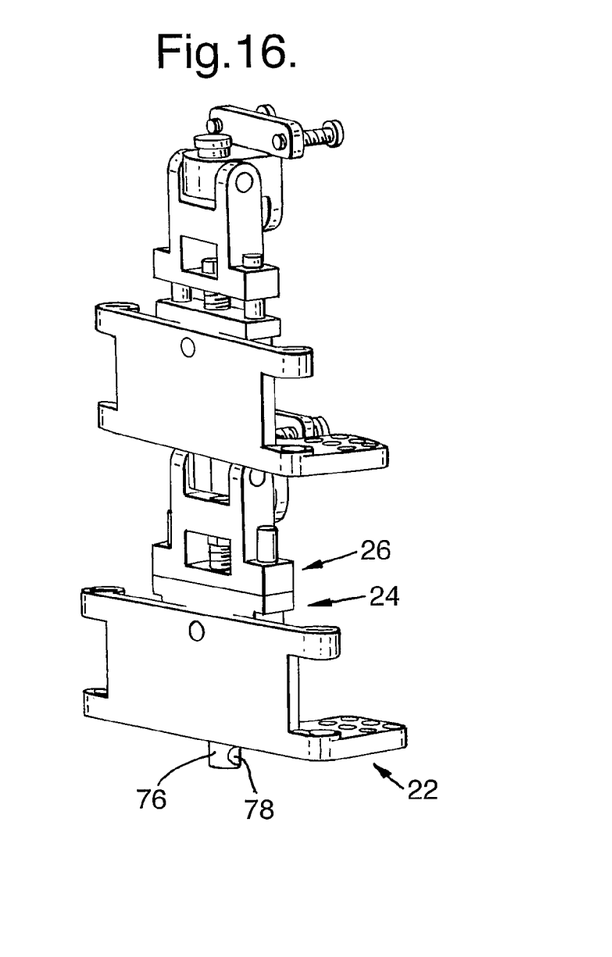
FIG. 16 is an isometric view of the segment group of FIG. 14.
Figure 17:
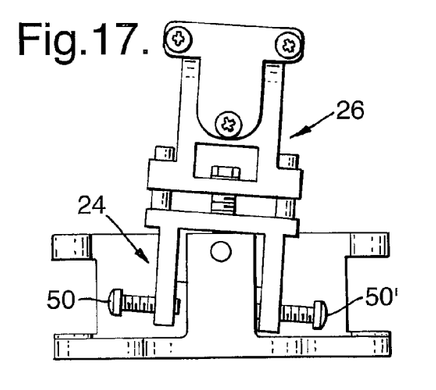
FIG. 17 illustrates the result of a spontaneous lateral torso tilt performed by the patient.
Figure 18:
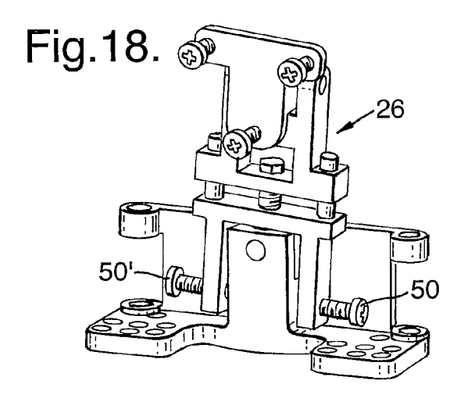
FIG. 18 is an isometric view of FIG. 17.
Figure 19:
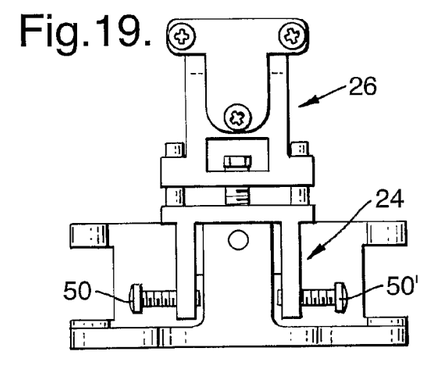
FIG. 19 shows the segment of FIG. 17 as restored to its original shape.
Figure 20:
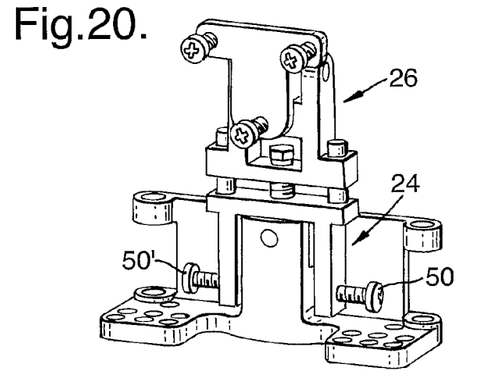
FIG. 20 is an isometric view of FIG. 17.

FIGS. 14 to 16 illustrate a twisting motion between the separate segmental units 20 (FIG. 3). By opening screw 82 and turning down screw 82' of one segmental unit 20, the adjacent segmental unit 20 is imparted a twist.

Figures 25, 26:
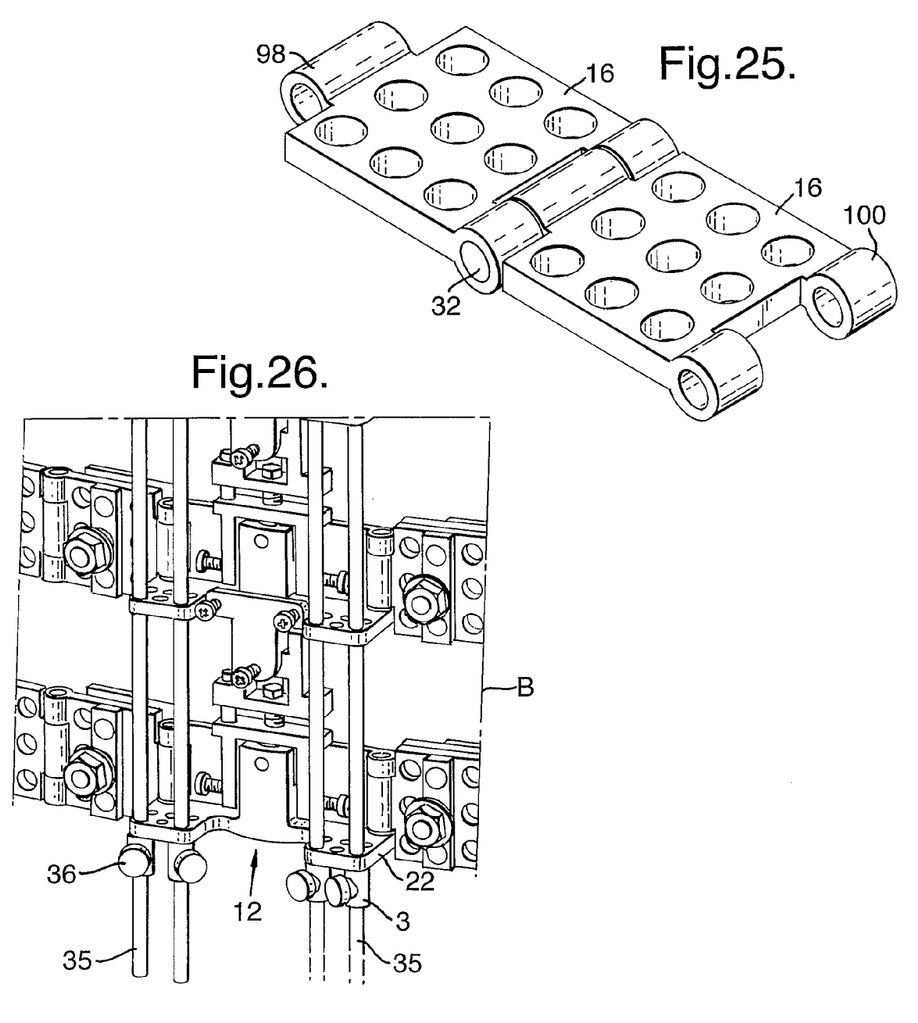
FIG. 25 is an isometric view of the belt elements of FIG. 24.
FIG. 26 is an enlarged view of detail B in FIG. 2, showing the elastically deformable biasing means.

FIGS. 17 to 20 shown the results of a spontaneous lateral torso tilt performed by the patient, with screws 50, 50' withdrawn. Return of the device to its original position (FIG. 19) is effected by action of the patient as assisted by the elastic means 35 as seen in FIG. 26.

Figure 21:
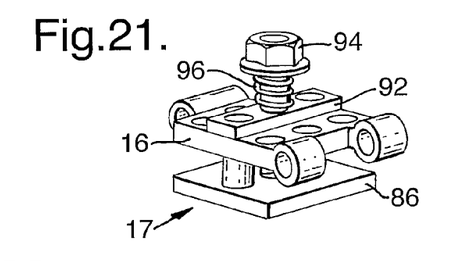
FIGS. 21 to 23 show one of the special belt elements in three of its limit positions.
Figure 22:
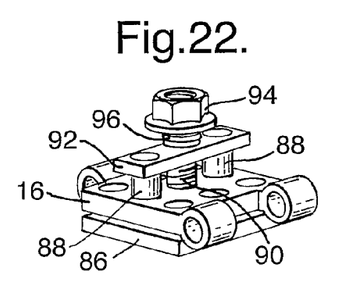
Figure 23:
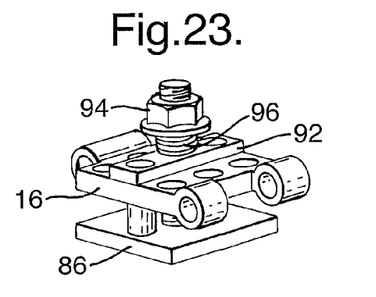

The special belt elements 17 are seen in FIGS. 21 to 23. They comprise a standard belt element 16, a plate 86, whereby pressure can be applied to selected points of the torso, two guide rods 88 for guiding belt element 16, which is freely moving along them, a threaded bolt 90 fixedly mounted on belt element 16, a cross member 92 fixedly attached to guide rods 88, a nut 94 engaging bolt 90 and a helical compression spring 96 interposed between nut 94 and cross member 92.

This arrangement has three limit positions: FIG. 21, in which nut 94 is almost unscrewed and pressure on plate 86 is minimal; FIG. 22 in which nut 94 has fully compressed spring 96, with belt element 16 quite close to plate 86, which can thus hardly rise, and FIG. 23 in which belt element 16 is totally locked.

Figure 24:
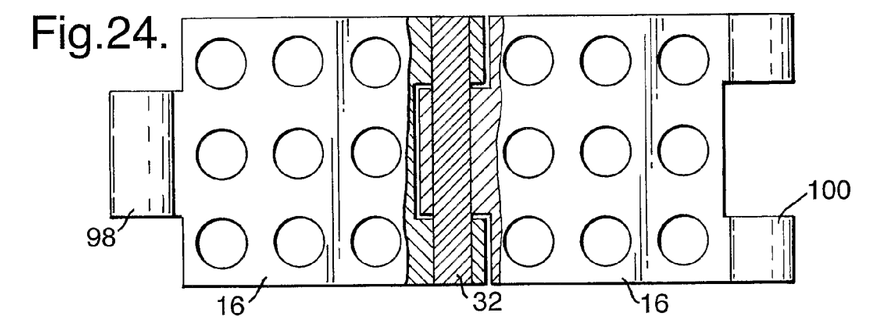
FIG. 24 represents two interlinked belt elements in partial cross-section.

In FIG. 24, in the partly cross-sectional view of a pair of interlinked belt elements 16 and their male and female hinge elements 98 and 100 respectively, it is seen that while the ends of hinge pin 32 are apparently a tight fit in the female hinge elements 100 to prevent its slipping out of the female hinge element, the diameter of its central section is slightly reduced to provide sufficient clearances for the belt elements 16 to move easily with respect to one another. Similar clearances are also provided between the male and female hinge elements 98 and 100. The holes in belt elements 16 serve to reduce their weight, except with the special belt elements 17, where the central traverse row of holes serve for the passage of guide rods 88 and the connection of threaded belt 90 (FIGS. 21 to 23). Not shown are paddings applied to the underside of belt elements 16.

Figure 2:
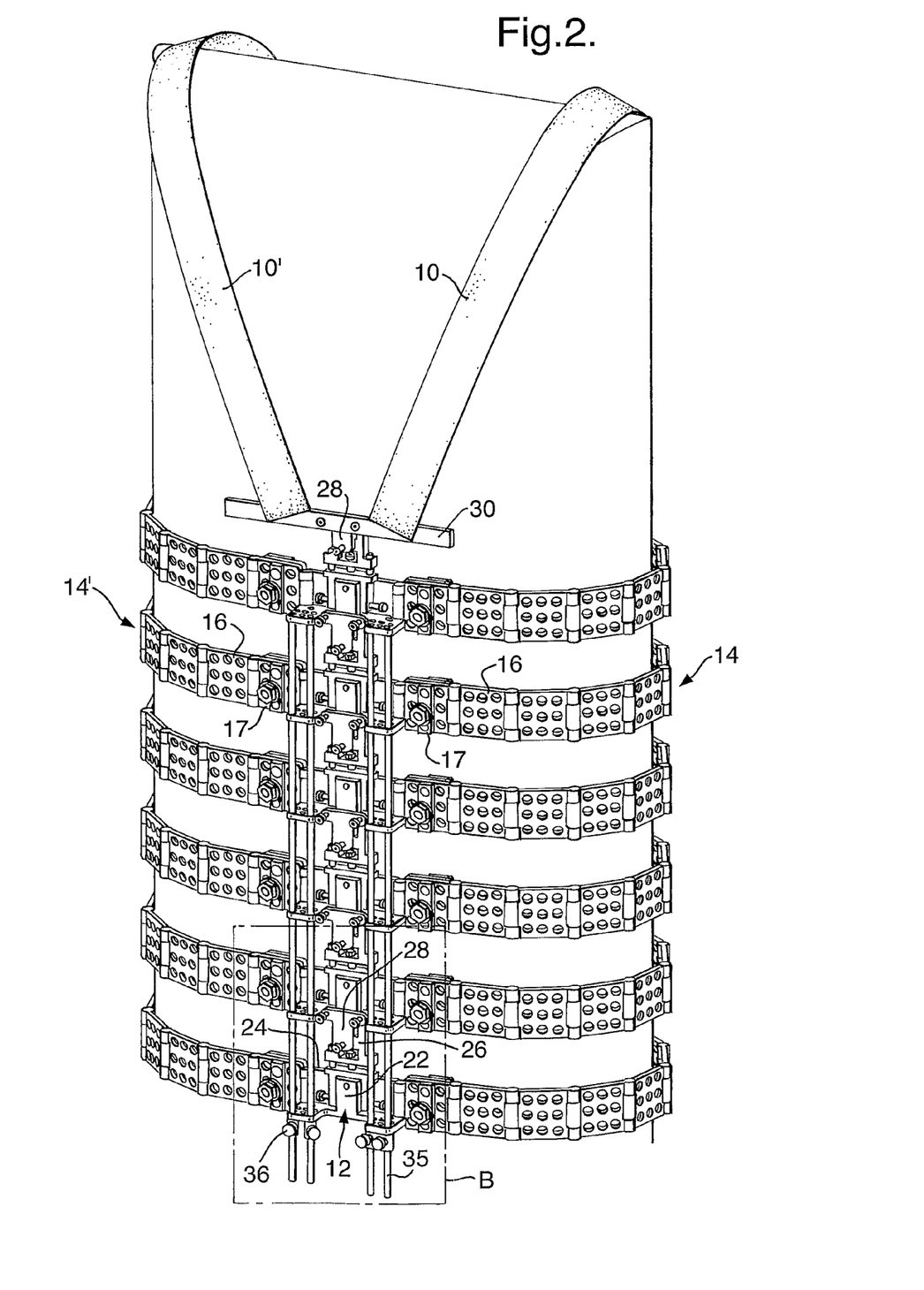
FIG. 2 represents an isometric view of the device.

FIG. 26, an enlarged rendering of detail B of FIG. 2 clearly shows the use of elastically deformable means, such as cords or springs 35 of which, for clarity, only two are shown on each side of sub-unit 22, although there are provided enough holes 34 for six cords 35.

While the embodiment discussed in the above dealt with the device attachable to the human torso only, it is envisioned to extend its applicability also to the extremities by providing straps or belts to encompass these extremities without undue pressures thereon, for the purpose of e.g., attaching further appliances to these straps or belts.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A customizable orthotic bracing device, comprising:
an exoskeletal quasi-spinal column extendable along the back of a patient and attachable to a body portion of said patient by means of a plurality of belt means substantially surrounding said body portion at different points thereof, with said quasi-spinal column being comprised of a plurality of stackable and interlinkable segmental units, each unit consisting of a number of interlinkable sub-units,
wherein the position of said interlinkable sub-units relative to one another can be adjusted in at least three degrees of freedom.

2. The orthotic device as claimed in claim 1, further comprising a plurality of elastically deformable means extending along said column and capable of acting on at least some of the sub-units of said segmental units.

3. The orthotic device as claimed in claim 1, wherein said belt means consists of pairs of belt halves, each comprised of a plurality of belt elements hingedly articulated to one another, each belt half having a first end and a second end, said first end being to a front part of said device, the second end being attached to a rear part of said device.

4. The orthotic device as claimed in claim 1, wherein the sub-units making up said segmental units are comprised of a first sub-unit, to which are hingedly attached the second ends of said belt halves, a second sub-unit which facilitates lateral tilt and linear translational movement, a third sub-unit co-acting with said second sub-unit in facilitating linear translational movement and co-acting with at fourth sub-unit in facilitating tilt in a median plane, said fourth sub-unit also facilitating a relative twisting movement involving said first sub-unit.

5. The orthotic device as claimed in claim 1, wherein said second sub-unit is provided with two counteracting screws which, between them, produce and define a position of lateral tilt of its own and all higher segmental units.

6. The orthotic device as claimed in claim 4, wherein said third sub-unit is provided with a screw which produces and defines a linear, translational movement of next-higher segmental units of said column.

7. The orthotic device as claimed in claim 4, wherein said fourth sub-unit is provided with two counteracting screws which produce and define a twisting movement of the next-higher segmental units of said column.

8. The orthotic device as claimed in claim 4, wherein said fourth sub-unit is further provided with a single screw which produces and defines a tilt in the median plane of all next-higher segmental units of said column.

9. The orthotic device as claimed in claim 2, wherein said plurality of elastically deformable means are threaded through holes provided in said first sub-units, being anchored in the upper-most of said first sub-units and being clamped fast below the lower-most of said first sub-units.

10. The orthotic device as claimed in claim 3, wherein said belt elements have male and female ends which are interlinked by hinge pins.

11. The orthotic device as claimed in claim 2, wherein said elastically deformable means are in the form of rubber cords or helical tension springs.

12. The orthotic device as claimed in claim 1, further comprising a split breast plate made of a textile material.

13. The orthotic device as claimed in claim 11, wherein said split breast plate is joinable by a zipper-type fastener.

14. The orthotic device as claimed in claim 1, wherein said half belts are tightened around the patient's torso by means of buckles and straps.

15. The orthotic device as claimed in claim 11, wherein the integrity of said zipper when closed is secured by a plurality of clasps extending across said zipper and adapted to absorb lateral forces tending to pull apart said zipper joint.

16. The orthotic device as claimed in claim 3, wherein rear faces of said belt elements are provided with a padding layer.

* * * * *